United States Patent [19]

Theissen

[11] 4,001,005

[45] Jan. 4, 1977

[54] HERBICIDAL COMPOSITIONS COMPRISING HALOPHENOXY BENZOIC ACID ESTERS

[75] Inventor: Robert J. Theissen, Westfield, N.J.

[73] Assignee: Mobil Oil Corporation, New York, N.Y.

[22] Filed: May 12, 1975

[21] Appl. No.: 576,770

Related U.S. Application Data

[62] Division of Ser. No. 477,233, June 7, 1974, Pat. No. 3,907,866.

[52] U.S. Cl. .............................................. 71/108
[51] Int. Cl.$^2$ ...................................... A01N 9/24
[58] Field of Search ............................ 71/108, 111

[56] References Cited

UNITED STATES PATENTS

| | | | |
|---|---|---|---|
| 3,169,849 | 2/1965 | Lemin | 71/107 |
| 3,652,645 | 3/1972 | Theissen | 71/111 X |

*Primary Examiner*—Lewis Gotts
*Assistant Examiner*—Catherine L. Mills
*Attorney, Agent, or Firm*—Charles A. Huggett; Hastings S. Trigg

[57] ABSTRACT

Alkyl ($C_4$–$C_{12}$), cycloalkyl ($C_3$–$C_8$), and unsaturated hydrocarbyl ($C_3$–$C_{10}$) esters of 2-nitro-5-(halophenoxy)benzic acids comprise a class of compounds that are highly effective pre- and post-emergence herbicides.

7 Claims, No Drawings

HERBICIDAL COMPOSITIONS COMPRISING HALOPHENOXY BENZOIC ACID ESTERS

This is a division of application Ser. No. 477,233, filed June 7, 1974, now U.S. Pat. No. 3,907,866.

BACKGROUND OF THE INVENTION

1. Field of the Invention

This invention is concerned with certain phenoxybenzoic acid esters and their use as herbicides.

2. Description of the Prior Art

In U.S. Pat. No. 3,652,645, there is disclosed alkyl ($C_1$–$C_3$) esters of 2-nitro-5-(halophenoxy) benzoic acids as herbicides. Under some early-season weather conditions, especially when treated soil is splashed onto the lower leaves, contact injury may be seen. On soybeans, this may appear as crinkling of the lower leaves of young plants. On corn, the effect may be a discolored band on the lower blades. Occasionally, stunting may be observed. Crop injury under high soil moisture levels may not appear for 2 or 3 weeks and is temporary. The crop will grow out of it and yields are not adversely affected.

The transverse (chlorotic) band on corn blades presents a phytotoxic appearance that is evident on the plant throughout the early growing season. Such appearance, although not adversely affecting yield, can be offensive to many growers and could dissuade them from suing an otherwise effective herbicide. It is the discovery of this invention that the alkyl ($C_4$–$C_{12}$) and cycloalkyl ($C_3$–$C_8$) esters, as well as the unsaturated hydrocarbyl ($C_3$–$C_{10}$) esters, do not appear to give the phytotoxic appearance evidenced by the alkyl esters disclosed in U.S. Pat. No. 3,652,645.

SUMMARY OF THE INVENTION

This invention provides herbicidal compounds having the formula:

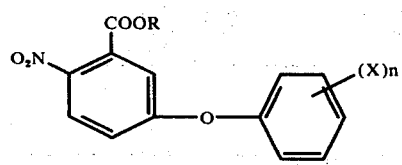

wherein X is halogen, $n$ is 1 to 3, and R is alkyl ($C_4$–$C_{12}$), cycloalkyl ($C_3$–$C_8$), or unsaturated hydrocarbyl ($C_3$–$C_{10}$).

It also provides the method for controlling plant growth by applying an herbicidal amount of such esters and, also, herbicidal compositions of such esters and a carrier.

DESCRIPTION OF SPECIFIC EMBODIMENTS

The compounds of this invention are readily prepared by reacting a 2-nitro-5-halophenoxybenzoyl chloride with the appropriate alcohol in the presence of a tertiary amine acceptor for HCl, such as triethylamine and pyridine. The benzoyl chloride is prepared, in a first step by the Ullmann ether synthesis reaction between the alkali metal (Na, K) salt of a halophenol and a 5-halo (cl, Br)-2-nitrobenzoic acid, methyl ester, or salt. The 2-nitro-5-(halophenoxy)benzoic acid is then converted to the acyl chloride by well known methods, such as by reacting it with $PCl_5$, $PCl_3$, or $SOCl_2$. The salt (Na) of the benzoic acid is converted to the acyl halide by well known methods, such as by reacting it with $PCl_5$, $PCl_3$, $POCl_3$, or $SOCL_2$. If the methyl ester is used in Ullmann ether synthesis, it is hydrolyzed to the acid, which is converted to the acyl halide as aforedescribed. Such procedure is described and illustrated in U.S. Pat. No. 3,812,284, which is hereby incorporated herein by reference thereto. The 5-halo-2-nitrobenzoic acid is readily prepared by nitrating a m-halotoluene, followed by oxidation of the methyl group well-known procedures.

The esterifying alcohol, i.e., the source of the "R" group in the structural formula of the compounds of this invention, is an alkanol ($C_4$–$C_{12}$), a cycloalkanol ($C_3$–$C_8$), or an unsaturated hydrocarbyl alcohol ($C_3$–$C_{10}$). The alkanol can have a normal (straight) chain or it can have a branched chain. The cycloalkanol is a saturated carbocyclic alcohol having between 3 and 8 carbon atoms. It can have methyl substituents on the ring. The unsaturated hydrocarbyl alcohol contains a vinyl

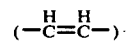

unsaturation or an acetylenic (—C ≡ C—) unsaturation. It can also contain a cyclohexyl group. Typical esterifying "R" groups contemplated are illustrated in the specific working examples.

SATURATED HYDROCARBYL ESTERS

The following example illustrates the preparation of a compound of this invention, wherein "R" is saturated, and demonstrates a method for product recovery.

EXAMPLE 1

Cyclohexyl 5-(2',4'-dichlorophenoxy)-2-nitrobenzoate

To a stirred solution of cyclohexanol (1.05g., 0.0105 mole) and triethylamine (1.10g., 0.011 mole) in toluene (30 ml.) was added 5-(2',4'-dichlorophenoxy)-2-nitrobenzoyl chloride (3.47g., 0.01 mole). A precipitate of triethylamine hydrochloride occurred immediately. The reaction solution was heated to reflux for one hour, cooled and diluted with diethyl ether (150 ml.). After filtering the triethylamine hydrochloride, the solvent was evaporated to give 4.1g. of a brown oil. A small amount of additional precipitate was filtered off. The ether was again stripped to yield 3.5g. of brown oil.

I.R. (neat): $\nu C{=}O$ 1725 cm$^{-1}$.

By a similar procedure, the compounds in the following list were also prepared.

EXAMPLES 2 through 18

2. n-Pentyl 5-(2',4'-Dichlorophenoxy)-2-nitrobenzoate, oil.
3. n-Butyl 5-(2',4'-Dichlorophenoxy)-2-nitrobenzoate, oil.
4. sec-Butyl 5-(2,'4'-Dichlorophenoxy)-2-nitrobenzoate, oil.
5. iso-Butyl 5-(2',4'-Dichlorophenoxy)-2-nitrobenzoate, oil.
6. Dodecyl 5-(2',4'-Dichlorophenoxy)-2-nitrobenzoate, oil.
7. 2-Octyl 5-(2',4'-Dichlorophenoxy)-2-nitrobenzoate, oil.

8. Isoamyl 5-(2',4'-Dichlorophenoxy)-2-nitrobenzoate, oil.
9. n-Octyl 5-(2',4'-Dichlorophenoxy)-2-nitrobenzoate, oil.
10. t-Butyl 5-(2',4'-Dichlorophenoxy)-2-nitrobenzoate, oil.
11. 2-Decyl 5-(2',4'-Dichlorophenoxy)-2-nitrobenzoate, oil.
12. 2-Heptyl 5-(2',4'-Dichlorophenoxy)-2-nitrobenzoate, oil.
13. 2-Nonyl 5-(2',4'-Dichlorophenoxy)-2-nitrobenzoate, oil.
14. n-Phentyl 2-Nitro-5-(2',4',6'-trichlorophenoxy)-benzoate, oil.
15. 2-Octyl 2-Nitro-5-(2',4',6'-trichlorophenoxy)-benzoate, oil.
16. Cyclohexyl 2-Nitro-5-(2',4',6'-trichlorophenoxy) benzoate, oil.
17. 2Octyl 5-(2',4'-Dichloro-6'-fluorophenoxy)-2-nitrobenzoate, oil.
18. Cyclohexyl 52',4'-Dichloro-6'-fluorophenoxy)-2-nitrobenzoate, oil.

HERBICIDAL EFFECTIVENESS
Method of Propagating Test Species

| | |
|---|---|
| Crabgrass | *Digitaria sanguinalis* |
| Johnson grass | *Sorgum Halepense* |
| Barnyard grass | *Echinochloa crus-galli* |
| Field bindweed | *Convolvulus arvensis* |
| Velvet leaf | *Abutilon theophrasti* |
| Turnip | *Brassica sp.* |
| Cotton | *Gossypium hirsutum* var. DPL smooth leaf |
| Corn | *Zea Mays* var. Golden Bantam |
| Bean | *Phaseolus vulgaris* var. Black Valentine |

All crop and weed species are planted individually in 3 inch plastic pots containing potting soil. Four seeds of each of corn, cotton, and snapbeans are seeded to a depth equal to the diameter of the seed. All other species are surface seeded and sprinkled with screened oil in an amount sufficient to cover the seeds. Immediately after planting, all pots are watered by sub-irrigation in greenhouse trays. Pots for the pre-emergence phase are seeded one day before treatment.

Planting dates for the post-emergence phase are varied so that all the seedlings will reach the desired stage of development simultaneously. The proper stage of seedling development for treatment in the post-emergence phase is as follows:

| | |
|---|---|
| GRASSES: | 2 inches in height |
| PIGWEED, BINDWEED, VELVET LEAF & TURNIPS: | 1 or 2 true leaves visible above cotyledons |
| COTTON: | first true leaf 1 inch in length; expanded cotyledons |
| CORN: | 3 inches-4 inches in height |
| BEANS: | primary leaves expanded; growing point at primary leaf node. |

Method of Treatment

Spray applications are made in a hood containing a movable belt and fixed spray nozzle. For passage through the spray hood, one pot of each species (pre-emergence phase) is placed on the forward half of a wooden flat and one pot of established plants (post-emergence phase) is placed on the rear half of the flat. Treatments are moved to the greenhouse after spraying. Watering during the observation period is applied only by sub-irrigation.

Compounds are screened initially at a rate of application equivalent to four to eight pounds per acre. Two weeks after treatment the pre- and post-emergence per cent injury is visually rated. Subsequent testing can be carried out at 2,1 and 0.5 pounds per acre.

Herbicidal testing of the compounds of Examples 1 through 18 showed the results (% control) set forth in Table I. A blank (-) indicates not tested. The plants are tabulated using the following abbreviations:

| | | | |
|---|---|---|---|
| Crabgrass | CG | Velvet leaf | VL |
| Johnson grass | JG | Turnip | TP |
| Barnyard grass | BG | Cotton | CT |
| Bindweed | BW | Corn | CN |
| | | Bean | BN |

TABLE I

| | | PRE/POST-EMERGENCE | | | | | | | |
|---|---|---|---|---|---|---|---|---|---|
| | | GRASSES | | | BROADLEAVES | | | CROPS | | |
| EXAMPLES | LBS./ACRE | CG | JG | BG | BW | Vl | TP | CT | CN | BN |
| 1. | 8 | 0/0 | 0/- | 0/- | 100/- | 90/- | 100/90 | 20/30 | 0/- | 0/90 |
| | 4 | 0/0 | 0/- | 0/- | 40/- | 70/- | 100/90 | 20/20 | 0/- | 0/100 |
| | 1 | 0/0 | 0/- | 0/- | 0/- | 0/- | 50/60 | 0/70 | 0/- | 0/100 |
| | 1/2 | 0/0 | 0/- | 0/- | 0/- | 0/- | 40/50 | 0/90 | 0/- | 0/80 |
| 2. | 8 | 0/0 | 0/- | 0/- | 30/- | 40/- | 70/90 | 0/70 | 0/- | 0/- |
| | 4 | 0/0 | 0/- | 0/- | 20/- | 20/- | 50/90 | 0/70 | 0/- | 0/90 |
| 3. | 8 | 60/0 | 30/- | 0/- | 30/- | 30/- | 70/90 | 0/60 | 0/- | 0/- |
| | 4 | 40/0 | 20/- | 0/- | 30/- | 20/- | 40/90 | 0/60 | 0/- | 0/60 |
| 4. | 8 | 0/0 | 0/- | 0/- | 0/- | 30/- | 90/100 | 0/70 | 0/- | 0/- |
| | 4 | 0/0 | 0/- | 0/- | 0/- | 0/- | 50/90 | 0/50 | 0/- | 0/80 |
| 5. | 8 | 0/0 | 20/- | 0/- | 50/- | 0/- | 20/70 | 20/30 | 0/- | 20/- |
| | 4 | 0/0 | 0/- | 0/- | 30/- | 0/- | 20/60 | 0/20 | 0/- | 20/80 |
| 6. | 8 | 0/0 | 0/- | 0/- | 40/- | 30/- | 70/90 | 0/100 | 0/- | 0/- |
| | 4 | 0/0 | 0/- | 0/- | 30/- | 20/- | 40/80 | 0/100 | 0/- | 0/60 |
| 7. | 8 | 0/0 | 0/- | 0/- | 80/- | 70/- | 90/100 | 20/100 | 0/- | 0/- |
| | 4 | 0/0 | 0/- | 0/- | 60/- | 60/- | 90/100 | 0/40 | 0/- | 0/100 |
| 8. | 8 | 0/0 | 0/- | 0/- | 70/- | 30/- | 90/90 | 20/100 | 0/- | 0/- |
| | 4 | 0/0 | 0/- | 0/- | 50/- | 20/- | 80/90 | 0/100 | 0/- | 0/80 |
| 9. | 8 | 0/0 | 0/- | 0/- | 0/- | 30/- | 70/90 | 0/100 | 0/- | 0/- |
| | 4 | 0/0 | 0/- | 0/- | 0/- | 20/- | 50/90 | 0/60 | 0/- | 0/100 |
| 10. | 8 | 80/- | 70/- | 50/- | 40/- | 70/- | 90/70 | 0/30 | 0/- | 30/- |
| | 4 | 70/0 | 30/- | 0/- | 0/- | 70/- | 90/60 | 0/30 | 0/- | 0/60 |
| 11. | 8 | 0/40 | 0/- | 0/- | 0/- | 70/- | 80/100 | 30/100 | 0/- | 0/- |
| | 4 | 0/0 | 0/- | 0/- | 0/- | 70/- | 70/90 | 0/100 | 0/- | 0/100 |
| 12. | 8 | 20/30 | 0/- | 0/- | 30/- | 90/- | 100/100 | 0/100 | 0/- | 50/100 |
| | 4 | 0/20 | 0/- | 0/- | 20/- | 70/- | 100/90 | 0/100 | 0/- | 0/100 |
| 13. | 8 | 0/40 | 0/- | 0/- | 40/- | 70/- | 90/100 | 0/100 | 0/- | 50/100 |

TABLE I-continued

| EXAMPLES | LBS./ACRE | PRE/POST-EMERGENCE | | | | | | | | |
|---|---|---|---|---|---|---|---|---|---|---|
| | | GRASSES | | | BROADLEAVES | | | CROPS | | |
| | | CG | JG | BG | BW | VI | TP | CT | CN | BN |
| | 4 | 0/40 | 0/- | 0/- | 20/- | 60/- | 70/90 | 0/100 | 0/- | 0/100 |
| 14. | 8 | 20/20 | 20/- | 20/- | -/- | -/- | 100/100 | 50/100 | 0/60 | 100/50 |
| | 2 | -/- | -/- | -/- | -/- | -/- | 50/80 | -/- | -/- | -/- |
| 15. | 8 | 0/0 | 0/- | 0/- | 0/- | -/- | 80/100 | 0/40 | 0/- | 0/80 |
| | 4 | 0/0 | 0/- | 0/- | 0/- | -/- | 0/100 | 0/20 | 0/- | 0/50 |
| 16. | 8 | 20/40 | 30/- | 0/- | 100/- | -/- | 100/90 | 0/90 | 0/- | 0/20 |
| | 4 | 0/- | 0/- | 0/- | 40/- | -/- | 90/100 | 0/90 | 0/- | 0/20 |
| | 2 | 0/- | 0/- | 0/- | 0/- | -/- | 90/90 | 0/20 | 0/- | 0/20 |
| 17. | 8 | 0/30 | 0/- | 0/- | 90/0 | -/- | 100/100 | 0/100 | 0/- | 0/100 |
| | 4 | 0/0 | 0/- | 0/- | 40/- | -/- | 90/100 | 0/100 | 0/- | 0/90 |
| 18. | 8 | 30/0 | 30/- | 30/- | 40/- | -/- | 100/100 | 0/100 | 0/- | 0/50 |
| | 4 | 0/0 | 0/- | 0/- | 0/- | -/- | 90/100 | 0/90 | 0/- | 0/30 |

CORN LEAF PHYTOTOXICITY COMPARISON TESTS

Under rainfall conditions, anything more than a very light drizzle, the halophenoxybenzoate ester herbicide can readily be splashed into the whorl of young (1–10 day old) corn seedlings. As the leaves grow out, the phytotoxicity is observed as a chlorotic transverse band across the leaf occurring at the previous point of contact in the corn whorl.

In order to demonstrate the considerably less phytotoxic nature of $C_4$ and greater alkyl esters as compared to $C_3$ and less esters, the following greenhouse corn leaf toxicity tests were conducted. These tests served as a screening procedure in simulating the phytotoxicity which occurs under actual field use conditions.

Test Method — Test solutions of the candidate compounds were prepared as follows 30 ppm – 3.0 mg of compound dissolved in 10.0 ml. of acetone. This was then diluted with 90.0 ml. of distilled water to give a cloudy colloidal suspension. 0.3 ppm – 1.0 ml. of the 30 ppm solution was diluted with 99.0 ml. of distilled water. (This concentration level is about the average water solubility limit of the test compounds and it more likely represents the actual field condition under which phytotoxicity occurs.)

One drop (ca, 0.05 ml.) of the test solution was then placed into the whorl of three (3) corn seedlings in the 2–3 leaf stage. The phytotoxicity ratings shown in the following Table II were taken 3 days after treatment. Examples 19–23 are reference comparisons of $C_3$ and lower esters.

Example 19 — Methyl 5-(2',4'-Dichlorophenoxy)-2-nitrobenzoate, mp 83°–5°C.

Example 20 — n-Propyl 5-(2',4'-Dichlorophenoxy)-2-nitrobenzoate, oil.

Example 21 — Isopropyl 5-(2',4'-Dichlorophenoxy)-2-nitrobenzoate, mp 55°–8°C.

Example 22 — Methyl 2-Nitro-5-(2',4',6'-trichlorophenoxy) benzoate, mp 68°–70°C.

Example 23 — Methyl 5-(2',4'-Dichloro-6'-fluorophenoxy)-2-nitrobenzoate, mp 68°–70°C.

TABLE II

CORN LEAF PHYTOTOXICITY RATINGS
5-Severe, 4-Moderate, 3-Mild, 2-Slight, 1-Trace, O-None

| EXAMPLE | Aqueous Solution Concentration | |
|---|---|---|
| | 30 ppm | 0.3 ppm |
| 1 | 1 | 1 |
| 2 | 3–4 | 2 |
| 3 | 3 | 0–2 |
| 4 | 3–4 | 0–2 |
| 5 | 3–4 | 0–2 |
| 6 | 2 | 0 |
| 7 | 2–3 | 0 |
| 8 | 3–4 | 0–1 |
| 9 | 2–3 | 0 |
| 10 | 2–3 | 0–2 |
| 11 | 0–2 | 0 |
| 12 | 3 | 0 |
| 13 | 0–3 | 0–1 |
| 14 | — | — |
| 15 | 0–1 | 0–1 |
| 16 | 0–3 | 0 |
| 17 | 0 | 0 |
| 18 | 0–2 | 0 |
| 19 | 5 | 4–5 |
| 20 | 3–4 | 3 |
| 21 | 4–5 | 3–4 |
| 22 | 4–5 | 4–5 |
| 23 | 5 | 4–5 |

Unsaturated Hydrocarbyl Esters

The preparation of compounds of this invention wherein the "R" group is unsaturated hydrocarbyl is illustrated in the following examples. A typical product separation technique is demonstrated.

EXAMPLE 24

3-Butyn-2-yl 5-(2',4'-dichlorophenoxy)-2-nitrobenzoate

To a stirred solution of 3-butyn-2-ol (15g., 2.15 mole) and triethylamine (253g., 2.5 mole) in toluene (1500 ml.) was added 5-(2',4'-dichlorophenoxy)-2-nitrobenzoyl chloride (500g., 1.44 mole). A precipitate of triethylamine hydrochloride formed immediately and the reaction exothermed to about 75°C. The solution was then heated at 60°C. for 15 hours. The solution was cooled and the precipitate filtered off. The filtrate was freed of solvent and excess triethylamine to give a brown oily product (561g.).

I.R. (neat): $\nu$C ≡ CH 3250, $\nu$C=O 1735 cm$^{-1}$

Utilizing a similar procedure, the compounds in the following list were also prepared.

Examples 25 through 36

25. Propen-2-yl 5-(2',4'-Dichlorophenoxy)-2-nitrobenzoate, oil.

26. Buten-2-yl 5-(2',4'-Dichlorophenoxy)-2-nitrobenzoate, oil.

27. 2-Methyl-3-buten-2-yl 5-(2',4'-Dichlorophenoxy)-2-nitrobenzoate, oil.

28. Propyn-2-yl 5-(2',4'-Dichlorophenoxy)-2-nitrobenzoate, oil.

29. 2-Methyl-3-butyn-2-yl 5-(2',4'-Dichlorophenoxy)-2-Nitrobenzoate, oil 30. 1-Methyl-1-ethylpropyn-2-yl 5-(2',4'-Dichlorophenoxy)-2-nitrobenzoate, oil.

31. 1-Pentyl-2-propynyl 5-(2',4'-Dichlorophenoxy)-2-nitrobenzoate, oil.

32. 1-Ethynylcyclohexyl 5-(2',4'-Dichlorophenoxy)-2-nitrobenzoate, oil.

33. Propyn-2-yl 2-Nitro-5-(2',4',6'-trichlorophenoxy) benzoate, oil.

34. 3-Butyn-2-yl 2-Nitro-5-(2',4',6'-trichlorophenoxy) benzoate, oil.

35. Propyn-2-yl 5-(2',4'-dichloro-6'-fluorophenoxy)-2-nitrobenzoate, oil.

36. 3-Butyn-2-yl 5-(2',4'-dichloro-6'-fluorophenoxy)-2-nitrobenzoate, oil.

The herbicidal effectiveness of the compounds of Examples 24–36 for Herbicidal Effectiveness is shown in the following Table III.

TABLE III
PRE/POST EMERGENCE

| EXAMPLE | LBS./ACRE | GRASSES | | | BROADLEAVES | | | CROPS | | |
|---|---|---|---|---|---|---|---|---|---|---|
| | | CG | JG | BG | BW | VL | TP | CT | CN | BN |
| 24. | 8 | 30/0 | 0/- | 0/- | 40/- | 90/- | 100/80 | 0/100 | 0/- | -0/90 |
| | 4 | 30/30 | 0/- | 40/- | 60/- | 80/- | 100/100 | 20/20 | 0/- | 30/90 |
| | 2 | 0/0 | 0/- | 0/- | 100/- | 70/- | 90/90 | 0/90 | 0/- | 0/100 |
| | 1 | 0/0 | 0/- | 0/- | 0/- | 50/- | 70/60 | 1/90 | 0/- | 0/100 |
| 25. | 8 | 80/30 | 70/- | -/- | -/- | -/- | 0/100 | -/90 | -/- | -/80 |
| 26. | 8 | 0/50 | 0/- | 0/- | 20/- | 60/- | 80/100 | 20/100 | 0/- | 0/100 |
| | 4 | 0/40 | 0/- | 0/- | 0/- | 50/- | 70/90 | 0/60 | 0/- | 0/80 |
| 27. | 8 | 0/40 | 0/- | 0/- | 0/- | 70/- | 70/50 | 0/0 | 0/- | 0/60 |
| | 4 | 0/20 | 0/- | 0/- | 40/- | 30/- | 0/40 | 0/0 | 0/- | 0/30 |
| 28. | 8 | 30/0 | 0/- | 0/- | 60/- | 50/- | 70/90 | 0/100 | 0/- | 0/100 |
| | 4 | 0/0 | 0/- | 0/- | 50/- | 40/- | 70/0 | 30/100 | 0/- | 30/100 |
| 29. | 8 | 50/0 | 0/- | 30/- | 0/- | 70/- | 100/90 | 40/100 | 0/- | 0/100 |
| | 4 | 20/0 | 20/- | 0/- | 30/- | 80/- | 90/- | 20/70 | 0/- | 0/50 |
| | 2 | 30/0 | 0/- | 0/- | 70/- | 80/- | 100/90 | 0/20 | 0/- | 0/100 |
| 30. | 8 | 90/0 | 50/- | 30/- | 30/- | 100/90 | 100/90 | 20/60 | 0/- | 0/90 |
| | 4 | 80/0 | 20/- | 0/- | 0/- | 80/- | 100/80 | 0/40 | 0/- | 0/30 |
| | 2 | 0/0 | 0/- | 0/- | 0/- | 30/- | 40/80 | 0/30 | 0/- | 0/20 |
| 31. | 8 | 0/30 | 0/- | 0/- | 0/- | 50/- | 30/60 | 0/40 | 30/- | 30/80 |
| 32. | 8 | 0/0 | 0/- | 0/- | 30/- | -/- | 90/80 | 0/20 | 0/- | 0/100 |
| 33. | 8 | 60/30 | 40/- | 30/- | 0/- | -/- | 50/90 | 0/30 | 0/- | 0/80 |
| | 4 | 40/0 | 0/- | 20/- | 0/- | -/- | 20/90 | 0/30 | 0/- | 0/40 |
| 34. | 8 | 0/0 | 0/- | 0/- | 0/- | -/- | 80/100 | 0/40 | 0/- | 0/90 |
| | 4 | 0/0 | 0/- | 0/- | 0/- | -/- | 50/90 | 0/30 | 0/- | 0/80 |
| 35. | 8 | 90/30 | 40/- | 50/- | 0/- | -/- | 100/100 | 0/100 | 0/- | 0/50 |
| | 4 | 90/20 | 0/- | 0/- | 0/- | -/- | 90/100 | 0/90 | 0/- | 0/30 |
| 36. | 8 | 90/40 | 60/- | 30/- | 90/- | -/- | 100/100 | 0/100 | 0/- | 0/30 |
| | 4 | 80/30 | 70/- | 0/- | 80/- | -/- | 100/100 | 0/90 | 0/- | 0/0 |

The compounds of this invention can be applied in various ways to achieve herbicidal action. They can be applied per se, as solids or in vaporized form, but are preferably applied as the toxic components in pesticidal compositions of the compound and a carrier. These compositions are preferably applied directly to the soil and incorporated therewith. The compositions can be applied, as granulars or dusts; as liquid sprays, or as gas-propelled sprays and can contain, in addition to a carrier, additives such as emulsifying agents, binding agents, gases compressed to the liquid state, odorants, stabilizers, and the like. A wide variety of liquid and solid carriers can be used. Non-limiting examples of solid carriers include talc, bentonite, diatomaceous earth, pyrophyllite, fullers earth, gypsum, flours derived from cotton seeds and nut shells, and various natural and synthetic clays having a pH not exceeding about 9.5. Non-limiting examples of liquid carriers include water, organic solvents such as alcohols, ketones, amides and esters, mineral oils such as kerosene, light oils, and medium oils and vegetable oils such as cottonseed oil.

In practice, herbicidal application is measured in terms of pounds of herbicide applied per acre. The compounds of this invention are effective herbicides when applied in herbicidal amounts, i.e., at rates between about 0.2 pound and about 10 pounds per acre.

Although the present invention has been described with preferred embodiments, it is to be understood that modifications and variations may be resorted to, without departing from the spirit and scope of this invention, as those skilled in the art will readily understand. Such modifications and variations are considered to be within the purview and scope of the appended claims.

What is claimed is:

1. A herbicidal composition comprising a carrier and a herbicidal amount of a compound having the formula:

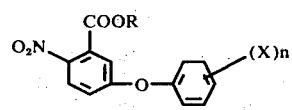

wherein X is halogen, $n$ is 1 to 3, and R is alkyl ($C_4$–$C_{12}$), cycloalkyl ($C_3$–$C_8$), or unsaturated hydrocarbyl ($C_3$–$C_{10}$).

2. The composition of claim 1, wherein said compound is Cyclohexyl 5-(2',4'-dichlorophenoxy)-2-nitrobenzoate.

3. The composition of claim 1, wherein said compound is 2-Octyl 5-(2',4'-dichlorophenoxy)-2-nitrobenzoate.

4. The composition of claim 1, wherein said compound is Cyclohexyl 2-Nitro-5-(2',4',6'-trichlorophenoxy)benzoate.

5. The composition of claim 1, wherein said compound is 3-Butyn-2-yl 5-(2',4'-dichlorophenoxy)-2-nitrobenzoate.

6. The composition of claim 1, wherein said compound is 2-Methyl-3-butyn-2-yl 5-(2',4'-dichlorophenoxy)-2-nitrobenzoate.

7. The composition of claim 1, wherein said compound is 3-Butyn-2-yl 5-(2',4'-dichloro-6'-fluorophenoxy)-2-nitrobenzoate.

* * * * *

UNITED STATES PATENT AND TRADEMARK OFFICE
CERTIFICATE OF CORRECTION

PATENT NO. : 4,001,005
DATED : January 4, 1977
INVENTOR(S) : ROBERT J. THEISSEN

It is certified that error appears in the above–identified patent and that said Letters Patent are hereby corrected as shown below:

Abstract, line 3      "benzic" should be --benzoic--

Col. 1, line 30      "suing" should be --using--

Col. 1, line 65      "(cl, Br)" should be --(Cl, Br)--

Signed and Sealed this

Third Day of May 1977

[SEAL]

Attest:

RUTH C. MASON
*Attesting Officer*

C. MARSHALL DANN
*Commissioner of Patents and Trademarks*

Disclaimer 4,001,005.—*Robert J. Theissen*, Westfield, N.J. HERBICIDAL COMPOSITIONS COMPRISING HALOPHENOXY BENZOIC ACID ESTERS. Patent dated Jan. 4, 1977. Disclaimer filed Feb. 9, 1979, by the assignee, *Mobil Oil Corporation*.

The term of this patent subsequent to Mar. 28, 1989, has been disclaimed.
[*Official Gazette June 19, 1979.*]